(12) United States Patent
Campbell

(10) Patent No.: US 8,026,266 B2
(45) Date of Patent: Sep. 27, 2011

(54) TREATMENT OF LENGTH DEPENDENT NEUROPATHY

(75) Inventor: James N. Campbell, Luthersville, MD (US)

(73) Assignee: Arcion Therapeutics, Inc., Baltimore, MD (US)

( * ) Notice: Subject to any disclaimer, the term of this patent is extended or adjusted under 35 U.S.C. 154(b) by 1058 days.

(21) Appl. No.: 11/557,455

(22) Filed: Nov. 7, 2006

(65) Prior Publication Data

US 2007/0142385 A1 Jun. 21, 2007

Related U.S. Application Data

(60) Provisional application No. 60/734,423, filed on Nov. 8, 2005.

(51) Int. Cl.
*A61K 31/44* (2006.01)
*A61K 31/54* (2006.01)
*A61K 31/415* (2006.01)
*A61K 31/505* (2006.01)
*A61K 31/425* (2006.01)
*A01N 43/40* (2006.01)
*A01N 43/50* (2006.01)
*A01N 43/54* (2006.01)
*A01N 43/78* (2006.01)

(52) U.S. Cl. ............... 514/392; 514/275; 514/227.2; 514/336; 514/370; 514/397; 514/398; 514/352

(58) Field of Classification Search .............. 514/392, 514/275, 227.2, 336, 370, 398, 397, 352
See application file for complete search history.

(56) References Cited

U.S. PATENT DOCUMENTS

| | | | |
|---|---|---|---|
| 4,201,211 A | 5/1980 | Chandrasekaran et al. | |
| 4,250,191 A | 2/1981 | Edwards | |
| 4,310,535 A | 1/1982 | Pierpaoli | |
| 4,443,441 A | 4/1984 | Galin | |
| 4,557,934 A | 12/1985 | Cooper | |
| 4,742,054 A | 5/1988 | Naftchi | |
| 4,746,509 A | 5/1988 | Haggiage et al. | |
| 4,801,587 A | 1/1989 | Voss et al. | |
| 5,070,084 A | 12/1991 | Campbell | |
| 5,447,947 A | 9/1995 | Campbell | |
| 6,054,461 A | 4/2000 | Fairbanks et al. | |
| 6,143,278 A * | 11/2000 | Elkhoury | 424/45 |
| 6,147,102 A | 11/2000 | Borgman | |
| 6,534,048 B1 | 3/2003 | Borgman | |
| 6,559,186 B1 | 5/2003 | Campbell | |
| 6,864,271 B2 | 3/2005 | Bazan et al. | |
| 7,064,140 B2 | 6/2006 | Sunkel et al. | |
| 2004/0101582 A1 | 5/2004 | Wolicki | |
| 2004/0132824 A1 | 7/2004 | Gil et al. | |

FOREIGN PATENT DOCUMENTS

| | | |
|---|---|---|
| DE | 2920500 | 11/1980 |
| EP | 0 241 050 | 10/1987 |
| JP | 1 216 928 | 8/1989 |
| WO | WO 92/14453 | 9/1992 |
| WO | WO 2007/025613 | 3/2007 |

OTHER PUBLICATIONS

Epstein et al. 1997, Topical clonidine for orofacial pain: a pilot study. Journal of Orofacial Pain, vol. 11, No. 4, pp. 346-352.*
AIDS Patient Care, 2000, Gel for neuropathy studied. vol. 14, No. 6, p. 338.*
Ahlgren et al. 1993, Mechanical hyperalgesia in streptozotocin-diabetic rats is not sympathetically maintained. Brain Research, vol. 616, pp. 171-175.*
Khan et al. 2002, Role of Primary afferent nerves in allodynia caused by diabetic neuropathy in rats. vol. 114, No. 2, pp. 291-299.*
Alfuzosin: http://www.answers.com/topic/alfuzosin; [online] retrieved from the internet on Dec. 11, 2008; Jun. 25, 2003; 4 pages.
Bretylium Tosylate: http://www.medicinenet.com/bretylium_tosylate-injection/article.htm; [online] retrieved from the internet on Dec. 12, 2005; Mar. 2, 2005; 2 pages.
Captopril; http://www.answers.com/topic/captopril; [online] retrieved from the internet on Dec. 11, 2008; 9 pages.
Clonidine: http://www.answers.com/topic/clonidine; [online] retrieved from the internet on Dec. 12, 2008; Jul. 1, 2002; 8 pages.
Engelman, "Side effects of sympatholytic antihypertensive drugs", *Hypertension*, 11(3): II-30-33 (Suppl II) (1988).
Ergoloid Mesylates: http://web.archive.org/web/20071018155031/http://umm.edu/altmed/drugs/ergoloid-mesylates-048700.htm; [online] retrieved from the internet on Dec. 15, 2008; Oct. 18, 2007; 6 pages.

(Continued)

*Primary Examiner* — Paddy Padmanabhan
*Assistant Examiner* — Kara R McMillian
(74) *Attorney, Agent, or Firm* — Pabst Patent Group LLP

(57) ABSTRACT

Compositions, and methods of use thereof, are provided for the treatment of painful neuropathy by local or topical delivery of compounds that interact with α-adrenergic receptors, especially an alpha$_2$ adrenergic agonist such as clonidine, to the entire painful area such that the need for systemic dosing is minimized. The compounds are delivered to or adjacent to painful areas in patients with painful length dependent neuropathy, and other neuropathies that affect the pain signaling fibers in the skin. A preferred compound for the treatment of patients with length dependent neuropathy is clonidine applied in a transdermal patch, gel, ointment, lotion, liposomal formulation, cream, or emulsion, wherein the concentration is sufficient to provide an effective dose in the painful area or immediately adjacent areas.

14 Claims, 2 Drawing Sheets

OTHER PUBLICATIONS

Guanadrel: http://www.medicinenet.com/guanadrel-oral/article.htm; [online] retrieved from the internet on Dec. 12, 2008; Mar. 2, 2005; 2 pages.

Guanfacine: http://www.nlm.nih.gov/medlineplus/druginfo/meds/a682245.html; [online] retrieved from the internet on Dec. 11, 2008; Jul. 1, 2002; 6 pages.

Harich Comparative Pain Scale: http://www.tipna.org/info/documents/ComparativePainScale.htm [online] retrieved from the internet on Dec. 11, 2008; Jul. 2002; 4 pages.

Indoramin: http://www.netdoctor.co.uk/medicines/I00000841.html. [online] retrieved from the internet on Dec. 11, 2008; Jun. 11, 2007; 5 pages.

Labetalol: http://www.answers.com/labetalol; [online] retrieved from the internet on Dec. 11, 2008; Jul. 1, 2002; 7 pages.

Medetomidine: http://www.answers.com/topic/medetomidine-1; [online] retrieved from the internet on Dec. 11, 2008; 4 pages.

Nefazodone: http://www.answers.com/topic/labetalol; [online] retrieved from the internet on Dec. 11, 2008; Oct. 25, 2004; 8 pages.

Nicergoline: http://www.nlm.nih.gov/medlineplus/druginfo/meds/a682346.html; [online] retrieved from the internet on Dec. 11, 2008; 4 pages.

Nitroglycerin Ointment: http://www.nlm.nih.gov/medlineplus/druginfo/meds/a682346.html; [online] retrieved from the internet Dec. 11, 2008; Apr. 1, 2003; 3 pages.

Phenoxybenzamine: http://www.nlm.nih.gov/medlineplus/druginfo/meds/a682059.html; [online] retrieved from the internet on Dec. 11, 2008; Apr. 1, 2003; 3 pages.

Phentolamine; http://www.answers.com/topic/phentolamine; [online] retrieved from the internet on Dec. 11, 2008; Jul. 1, 2002; 7 pages.

Prazosin; http://www.nlm.nih.gov/medlineplus/druginfo/meds/a682245.html; [online] retrieved from the internet on Dec. 11, 2008; Mar. 1, 2007; 3 pages.

Rauwolfia: http://www.answers.com/topic/rauwolfia; [online] retrieved from the internet on Dec. 11, 2008; 4 pages.

Reserpine: http://www.answers.com/topic/reserpine; [online] retrieved from the internet on Dec. 11, 2008; Jul. 1, 2002; 9 pages.

Trazodone: http://www.answers.com/topic/trazodone; [online] retrieved from the internet on Dec. 11, 2008; Jul. 1, 2002; 13 pages.

Campbell, et al., "Nerve lesions and the generation of pain", *Muscle Nerve*, 24(10):1261-73 (2001).

Clonidine (Systemic), "Clonidine Drug Information, Professional", pp. 2-14, revised May 21, 1999; (accessed Feb. 20, 2009).

Hardmen, et al., (ads.), "β-Adrenergic Agonists", in *The Pharmacological Basis of Therapeutics*, pp. 212-219 (1996).

Nakamura, et al., "Peripheral Modulation of Pain in Conscious Guinea Pigs: Effect of Morphine, Nalorphine, and Clonidine", *Brazilian J Med Biol Res*, 21:577-583 (1988).

Okumura, et al., "The selectivity of newly synthesized ergot derivatives to [alpha]1(subscript)- and [alpha]2(subscript)-adrenoceptors, D1(subscript)- and D2(subscript)-dopaminergic receptors, muscarinic acetylholinoceptors and [beta]-adrenoceptors", *Gen. Pharmac.*, 19(3):463-466 (1988).

Perhach, et al., "Antihypertensive activity of 2-amino-4-(3,4-dichlorophenyl)-2-imidazoline (MJ 10459-2) and catcholamine reduction", *Res. Communications in Chem Pathol and Pharmac*, 12(1):155-162 (1975).

Preifer, et al., "Topical Clonidine gel improves painful symptoms of diabetic neuropahy", in Abstracts are excerpts from 59th annual ADA meeting held from Jun. 19 to Jun. 22, 1999, San Diego, California, USA, *Int. J. Diab. Dev. Countries*, 10:123-124 (1999).

U.S. Appl. No. 11/123,257, filed May 5, 2005, Campbell.

"Curatek begins pivotal clinical study of new treatment for neuropathic pain", pp. 1-2, accessed Jun. 25, 2009, www.mult-sclerosis.org/news/Mar2000/ChonidineforNeuropathicPain.html, *Curatek Pharmaceuticals Press Release* (2000).

Abram, et al., "Treatment of long-standing causalgia with prazoin" *Regional Anesthesia* 6(2):79-81 (1981).

Berkow, *The Merck Manual of Diagnosis and Therapy, 15th Edition*, pp. 1347-1349, Merch & Co.: Rahway, N.J., 1987.

Davis, et al., "Topical application of clonidine relieves heperalgesia in patients with sympathetically maintained pain" *Pain* 47(3):309-317 (1991).

De Oliveira, et al., "Pain reaction after topical NA and lesions of the obex region in the alert guinea pig" *Physiology & Behavior* 28(3):413-416 (1982).

Ghostine, et al., "Phenoxybenzamine in the treatment of causaigia" *Journal of Neurosurgery* 60(6):1263-1268 (1984).

*Index Nominum 1987* pp. 284, Swiss Pharmaceutical Society: Zurich, CH, 1987.

Krieglstein, "The influence of topically applied bethanidine on intraocular pressure and pupil in the rabbit" *Graefes ARchiv. Ophthalmologie* 196(1):31-38 (1975).

Krieglstein, "The influence of bretylium tosylate on the intraocular pressure of the rabbit" *Graefes Archiv. Ophthalmologie* 197(2):153-158 (1975).

Loh and Nathan, "Painful peripheral states and sympathetic blocks" *J. Neurol. Neurosurg. Psychiat*. 41(7):664-671 (1978).

Merck Manual, Raynard's Phenomenon and Disease, Holvey, Ed. pp. 487 1972.

Byas-Smith, et al., "Transdermal clonidine compared to placebo in painful diabetic neuropathy using a two-stage 'enriched enrollment' design", *Pain*, 60(3):267-74 (1995).

Curtis and Marwah, "Evidence for alpha adrenoceptor modulation of the nociceptive jaw-opening reflex in rats and rabbits", *J. Pharmacol. Exp. Ther.*, 238(2):576-9 (1986).

Gonzales, et al., "Production of hyperalgesic prostaglandins by sympathetic postganglionic neurons", *J. Neurochem.*, 53(5):1595-8 (1989).

Goodman, et al., "The pharmaceutical basis of therapeutics", 6th Edition, Chapter 9, New York, MacMillan, pp. 176-210 (1980).

Hobelmann, et al., "Use of prolonged sympathetic blockade as an adjunct to surgery in the patient with sympathetic maintained pain", *Microsurgery*, 10(2):151-3 (1989).

Ishizuki, "Letter to the editor: clinical application of guanethidine ointment to the treatment of painful states and allodynia", *Clin. Jour. of Pain*, 261 (1988).

Ito, et al., "Effects of calcium antagonists on alpha-adrenoceptor mediated vasoconstrictions of the canine intermediate auricular artery", *Jpn. J. Pharmacol.*, 44(2):121-6 (1987).

Janig, "Causalgia and reflex sympathetic dystrophy: In which way is the sympathetic nervous system involved?", *Trends in Neurosciences*, 8(11):471-7 (1985).

Jarrott, et al., "Clonidine: understanding its disposition, sites and mechanism of action", *Clin. Exp. Pharmacol. Physiol.*, 14(5):471-9 (1987).

Loh and Nathan, "Painful peripheral states and sympathetic blocks", *J. Neurol. Neurosurg. Psychiatry*, 41(7):664-71 (1978).

Naftchi, *Chemical Abstracts*, 110(9):69410r.

Nakagawa, et al., *Chemical Abstracts*, 111(2):12526z.

Nakagawa, et al., *Chemical Abstracts*, 110(12):101838z.

Nakamura, et al., "Peripheral analgesic action of clonidine: mediation by release of endogenous enkephalin-like substances", *Eur. J. Pharmacol.*, 146(2-3):223-8 (1988).

Olin, et al., "Facts and comparisons", J.B. Lippincott Co., St. Louis, Mo., p. 162e (1988).

Peltier and Russell, "Recent advances in drug-induced neuropathies", *Curr. Opin. Nerology*, 15:633-638 (2002).

Price, et al., "Psychophysical observations on patients with neuropathic pain relieved by a sympathetic block", *Pain*, 36(3):273-88 (1989).

Raynard's Phenomenon and Disease Merck Manual, Hovey, Ed., p. 487 (1972).

Sagen and Proudfit, "Evidence for pain modulation by pre- and postsynaptic noradrenergic receptors in the medulla oblongata", *Brain Res.*, 331(2):285-93 (1985).

Singleton, "Evaluation and treatment of painful peripheral polyneuropathy", *Semin. Neurol.*, 25(2): 185-95 (2005).

Zeigler, et al., "Transdermal clonidine versus placebo in painful diabetic neuropathy", *Pain*, 48(3):403-8 (1992).

\* cited by examiner

TREATMENT OF LENGTH DEPENDENT NEUROPATHY

CROSS-REFERENCE TO RELATED APPLICATION

This application claims priority under 35 U.S.C. 119 to U.S. Ser. No. 60/734,423 filed Nov. 8, 2005 by James N. Campbell.

FIELD OF THE INVENTION

The invention is directed to the treatment of pain associated with length dependent and other neuropathies such as may result from diabetes and other conditions.

BACKGROUND OF THE INVENTION

Pain often develops from diseases that affect the somatosensory system. One disease that is often implicated is diabetes mellitus. Diabetes may affect the nervous system in different ways but one of the classical disorders is a length dependent neuropathy. Here axons with longer axons preferentially are involved in a neuropathy which is associated with both degeneration and a sensitization of nociceptors. The classic feature is burning pain typically involving the feet given that the axons to the feet represent the longest primary afferents in the body. This problem may occur early or late in the disease, and in fact may occur in so-called pre-diabetes which is a condition representing a disorder of glucose metabolism without strictly meeting the criteria for diabetes mellitus. It is now appreciated that diabetes is but one cause of a length dependent neuropathy. The painful symptoms that accompany these disorders, including an idiopathic small fiber neuropathy, are nearly identical with that seen in diabetes mellitus. Treatments directed at treatment of the diabetes mellitus itself may help slow the progression of the neuropathy but do not necessarily address the pain. There are no known treatments for idiopathic length dependent small fiber neuropathy. Certain chemotherapeutic drugs induce a length dependent neuropathy associated with pain. This pain may limit dosing and thus affect the adequacy of the cancer treatment. Systemic treatments of pain include use of opioids, anticonvulsants, antidepressants, and membrane stabilizers. All of these therapies are frequently ineffective and typically their use is accompanied by a substantial adverse side effect profile. Systemic therapies can be given by the oral route, or by patches applied to the skin. Lidocaine patches can be applied to the skin. Their value in treatment of pain associated with length dependent neuropathies is limited because of numbing of the skin. Capsaicin can be applied locally to the skin but application is associated with significant pain and the capsaicin destroys nociceptor function.

Some prior attempts also have been made to treat painful diabetic neuropathy with clonidine, a potent $\alpha_2$-adrenergic partial agonist used primarily for the treatment of hypertension (Jarrott et al., "Clonidine: Understanding its disposition, sites, and mechanism of action", Clin. Exp. Pharm. Physiol., 14, 471-479 (1987)). Clonidine has been applied topically to areas remote to the painful area as an alternative to oral delivery for effecting systemic delivery. For example, in a placebo-controlled cross-over pain trial in patients with painful diabetic neuropathy, no statistically significant difference between patients receiving systemic clonidine administered with transdermal patches and patients receiving placebo patches was observed (Zeigler et al. Pain 48: 403-408 (1992)). In a follow-up placebo controlled pain study in similar patients with painful diabetic neuropathy, transdermal patches delivering systemic levels of clonidine were evaluated using a two-stage enriched enrollment design (Byas-Smith et al. Pain 60: 267-274 (1995)). Only twelve of forty-one patients (29%) who completed the initial course of treatment were considered clonidine responders. These twelve clonidine responders were then rechallenged in a second placebo controlled study which used the highest dosage available with the transdermal patch system. The pain reduction relative to placebo tended to be modest although statistically significant. (p<0.015). The site of action of clonidine was not studied in this study. In principal the site of action could be central or peripheral. In other pain conditions a central analgesic action of clonidine has been determined. This treatment involved systemic delivery of clonidine with a transdermal patch applied remote to the painful area, resulting in systemic blood levels exceeding 0.2 ng/ml.

It is therefore an object of the present invention to provide methods and compositions to effectively treat or alleviate pain in length dependent or other neuropathies, as may be associated with diabetes, by topical local delivery to the painful area of an alpha-2 adrenergic agonist.

BRIEF SUMMARY OF THE INVENTION

Compositions, and methods of use thereof, are provided for the treatment of pain due to length dependent or other neuropathy by local or topical delivery of concentrations of compounds that interact with $\alpha$-2 adrenergic receptors, especially an alpha$_2$ adrenergic agonist such as clonidine, to the painful area, without producing systemically effective levels of the clonidine. The compounds are delivered to or adjacent to painful areas in patients with length dependent of other neuropathy that results in pain associated with disease or damage to the pain signaling primary afferent (sensory) fibers and their receptor, not sympathetically maintained pain. For example, in a patient with painful diabetic neuropathy where the complaint is burning pain in the feet the alpha-2 agonist is topically applied to the feet in the painful region. A preferred compound for the treatment of patients with diabetic neuropathy is clonidine applied in an ointment, gel, lotion, or transdermal patch, wherein the dosage is sufficient to provide an effective dose in the painful area or immediately adjacent areas, preferably without producing pharmacologically active systemic blood levels.

DETAILED DESCRIPTION OF THE INVENTION

I. Formulations

A. $\alpha_2$-adrenergic Agonists

Figure 1:
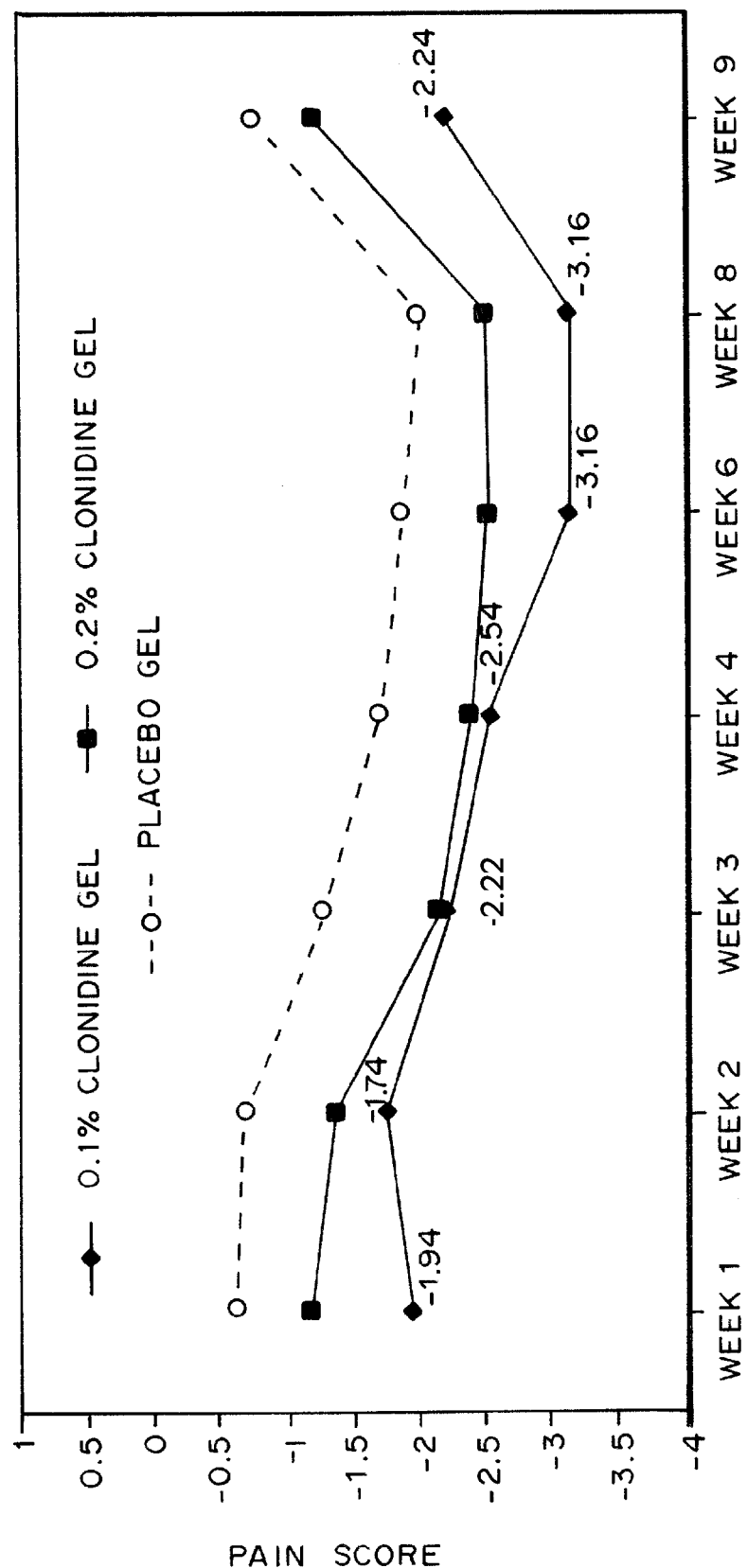
FIG. 1 is a graph of pain score over time (1-9 weeks) that shows the mean NGPS reduction by week, diamond, 0.1% clonidine; square, 0.2% clonidine, and circle, placebo.

The method of treating or reducing the symptoms (i.e. burning, pain) associated with length dependent neuropathies includes locally or topically administering an effective amount of an $\alpha_2$-adrenergic agonist or combination thereof. $\alpha_2$-adrenergic agonists are known to those skilled in the art. See, for example, The Pharmacological Basis of Therapeutics, 8th Edition, Gill, A. G., T. W. Rall, A. S. Nies, P. Taylor, editors (Pergamon Press, Co., Inc., NY 1990).

Agents with alpha-2 adrenoreceptor agonist activity are represented by

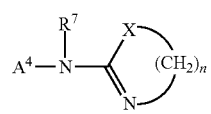

Formula I:

wherein $A^4$ may be selected from aryl, and heteroaryl, which may be substituted by one or more radicals selected from alkyl, branched alkyl, cycloalkyl, hydroxyl, alkoxy, cycloalkylalkyl, alkoxyalkyl, aryl, alkanoyl, alkoxycarbonyl, carboxyl, amino, cyano, halogen, thioalkyl, dialkylamino, arylamino, alkylsulfinyl, alkylsulfonyl, arylsulfinyl or arylsulfonyl; wherein X is selected from thio, imino, or methylene; wherein $R^7$ is selected from hydrogen, lower alkyl, or oxygen-containing heterocycle; and wherein n is either 2 or 3; or a pharmaceutically acceptable salt thereof.

A preferred class of compounds of Formula I consists of those compounds wherein $A^4$ is phenyl; wherein $A^4$ is substituted phenyl, on which positions 2 and 6 of the phenyl ring may be independently substituted by a radical selected from hydrogen, chloro, methyl, ethyl, or cycloalkyl, and positions 3, 4, and 5 may be independently substituted by a radical selected from hydrogen, methyl, trifluoromethyl, fluoro, or cyano; wherein $A^4$ is 3-thienyl, on which positions 2 and 4 are independently substituted by a radical selected from hydrogen, chloro, methyl, ethyl, or cycloalkyl; wherein $A^4$ is 1-naphthyl, 5,6,7,8-tetrahydronaphthyl-1-yl, pyrrolyl, oxazolyl, isoxazolyl, indol-3-yl, indazol-3-yl, quinolinyl, quinazolinyl, quinoxazolinyl, benzoxazolyl, and benzothiophen-3-yl; wherein $A^4$ is pyrimidin-4-yl, on which positions 3 and 5 are independently substituted by hydrogen, chloro, methyl, ethyl, cycloalkyl, or methoxy; wherein $R^7$ is either hydrogen or tetrahydropyran-2-yl; wherein X is thio or imino; and wherein n is 2.

An especially preferred class of compounds of Formula I consists of compounds wherein $A^4$ is selected from phenyl, 2,6-dichlorophenyl, 2,6-dimethylphenyl, 2,6-diethylphenyl, 3,4-dihydroxyphenyl, 3-fluoro-6-methylphenyl, 2-chloro-5-trifluoromethylphenyl, 2-chloro-4-methylphenyl, 3-chloro-4-methylthien-3-yl, 5,6,7,8-tetrahydronaphth-1-yl, and 4-chloro-5-methoxy-2-methylpyrimidin-4-yl; wherein $R^7$ is hydrogen or tetrahydropyran-2-yl; wherein X is thio or imino; and wherein n is 2.

A specifically preferred class of compounds of Formula I consists of xylazine, flutonidine, moxonidine, tramazoline, tolonidine, piclonidine, tiamenidine, and clonidine.

Although described above with reference specific to compounds, one can also utilize enantiomers, stereoisomers, metabolites, derivates and salts of the active compounds. Methods for synthesis of these compounds are known to those skilled in the art. Examples of pharmaceutically acceptable salts include, but are not limited to, mineral or organic acid salts of basic residues such as amines, and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Conventional non-toxic salts include those derived from inorganic acids such as hydrochloric, hydrobromic, sulfuric, sulfamic, phosphoric and nitric acid; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic and isethionic acids. The pharmaceutically acceptable salts can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed. (Mack Publishing Company, Easton, Pa., 1985, p. 1418).

A prodrug is a covalently bonded substance which releases the active parent drug in vivo. Prodrugs are prepared by modifying functional groups present in the compound in such a way that the modifications are cleaved, either in routine manipulation or in vivo, to yield the parent compound. Prodrugs include compounds wherein the hydroxy or amino group is bonded to any group that, when the prodrug is administered to a mammalian subject, cleaves to form a free hydroxyl or free amino, respectively. Examples of prodrugs include, but are not limited to, acetate, formate and benzoate derivatives of alcohol and amine functional groups.

A metabolite of the above-mentioned compounds results from biochemical processes by which living cells interact with the active parent drug or other formulas or compounds of the present invention in vivo. Metabolites include products or intermediates from any metabolic pathway.

B. Excipients

These compounds have previously been administered systemically (either orally, skin patch, or by injection). Systemic administration either does not work or requires high doses and is thus associated with systemic side effects such as fatigue, dizziness, tiredness, headache, constipation, nausea, vomiting, diarrhea, insomnia, and dry mouth. Topical administration is described for treatment of sympathetically maintained pain in U.S. Pat. No. 5,447,947 issued Sep. 5, 1995 to Campbell, and in U.S. Pat. Nos. 6,534,048 issued Mar. 18, 2003 to Borgman and 6,147,102 issued Nov. 15, 2000 to Borgman.

In the method described herein, the compounds are administered locally or topically directly to or adjacent the painful area, in a suitable pharmaceutical carrier, many of which are known to those skilled in the art. The carrier can be in the form of a lotion, ointment, gel, solution, or transdermal patch. Topical administration also includes iontophoresis wherein an electric current drives the drug, in the form of an ion such as a pharmaceutically acceptable salt, into the skin. The topical application allows the drug to reach high concentration at the painful area or tissue immediately adjacent thereto, avoiding many of the side effects of these compounds observed following systemic administration.

Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980). The active compounds (or pharmaceutically acceptable salts thereof) may be administered per se or in the form of a pharmaceutical composition wherein the active compound(s) is in admixture or mixture with one or more pharmaceutically acceptable carriers, excipients or diluents. Pharmaceutical compositions may be formulated in conventional manner using one or more physiologically acceptable carriers comprising excipients and auxiliaries which facilitate processing of the active compounds into preparations which can be used pharmaceutically.

C. Combination Therapies

The dosage formulation can be administered alone or in combination with a therapy such as an opioid, anticonvulsant, membrane stabilizer, and/or psychoactive drugs (for example, anti-depressants).

These may be formulated with the agonist in the pharmaceutically acceptable carrier for topical or local administration or administered in a separate formulation, with the other therapy being administered locally (by subcutaneous or intramuscular injection), topically or systemically, to the patient.

II. Methods of Administration

A. Patients to be Treated

A variety of diseases can affect the peripheral nervous system. Many of these disorders are not painful, but if the pain signaling system is affected, then pain may result. The prototype painful neuropathy stems from diabetes. The most common effects on the nervous system result from a length dependent neuropathy. This means that the longer the sensory axon the more likely the axon may be affected. Given that the axons that go to the feet are the longest primary afferents in the body, these fibers are affected first. As the disease progresses, other axons shorter in length are affected. The length dependent neuropathies may be caused by a variety of diseases. The most common (60-70%) is diabetes. These neuropathies may also be caused by kidney disease, hormonal imbalances, vitamin deficiencies, alcoholism, autoimmune disorders, toxins, chemotherapy, and infections (e.g., AIDS).

In a preferred embodiment, the treatment is given to patients with neuropathy that stems from diabetes mellitus. In another preferred embodiment, the treatment is administered to patients with a sensory peripheral neuropathy in the painful region. In yet another embodiment, the treatment is administered to a patient with a small fiber neuropathy in the painful region.

B. Dosages and Treatment Regimes

The dosage formulation is administered from once a week to several times a day, depending on the patient. In one embodiment, the therapeutic agent is clonidine administered in a concentration between 0.1 and 10% clonidine. The dose is determined by the region of pain. Because the effect of the clonidine is local it must be applied to the painful area. Thus in patients with broader areas of pain a higher dose of clonidine will be necessary though the percent concentration remains constant. The area treated is constrained by the systemic dosing. When 0.5% clonidine is applied to both feet, systemic effects may emerge as blood levels will approach those observed in treatment of hypertension. In the study done with 0.1% and 0.2% clonidine described below, the mean blood level was well below 0.1 ng/mg (one third of patients had no detectable clonidine in the blood), whereas the blood levels exceed 0.2 ng/ml with systemic delivery.

Example 1

Formulation of Neuclon™ (Clonidine) 0.1% Topical Gel

Neuclon™ (clonidine) 0.1% Topical Gel contains 0.1 mg of clonidine hydrochloride per 1.0 gram gel. The gel is formulated at pH 8.0 in order to maximize the amount of clonidine freebase in the product. Clonidine hydrochloride has a pKa of 8.2. The formulation is shown in Table 1.

TABLE 1

Formulation of Neuclon ™ (clonidine) 0.1% Topical Gel

| Ingredient | % (w/w) |
|---|---|
| Clonidine hydrochloride USP | 0.1% |
| Benzyl alcohol NF | 1.0% |
| Carbopol 980 NF | 0.6% |
| Sodium hydroxide NF | adjust to pH 8 |
| Hydrochloric acid NF | adjust to pH 8 (if necessary) |
| Purified water USP | qs ad 100% |

Example 2

Treatment of Patients with Painful Diabetic Neuropathy

The objective of this study was to test the analgesic effects of 0.1% and 0.2% topical clonidine gel compared to a placebo gel in patients with chronic, lower extremity, painful diabetic neuropathy.

Materials and Methods

One hundred sixty-six (166) adult patients with chronic, lower extremity, painful diabetic neuropathy who met the study admission criteria were enrolled in this multicenter study. Diabetic patients with a clinical diagnosis of neuropathy pain had to have an average daily pain score of 5 or greater on the 11-point Numerical Graphic Pain Scale (NGPS). Patients were allowed to continue using other medications for neuropathic pain, provided dosing with these medications was unchanged for 30 days prior to enrollment and during the study.

Patients were randomized to either 0.1% or 0.2% topical clonidine gel or placebo gel for this blinded, parallel design, 10-week study. Drug treatment lasted for 8 weeks, beginning with twice a day dosing for two weeks and escalating to three times a day for the remaining six weeks.

Analgesic efficacy was assessed on a weekly basis during the first month and biweekly during the second month by use of the following assessment instruments: Numerical Graphic Pain Scale (NGPS), Pain Relief Scale, Allodynia Scales for touching and cooling, Patient and Investigator Global Improvement assessments and Functional Interference Scales. Patients maintained daily outcome assessment diaries for the duration of the study.

Patient demographics for all three treatment groups were similar, as shown in Table 2.

TABLE 2

Patient demographics for all treatment groups

| Group | Age in Years (Range) | Gender | Diabetes Duration in Years (Range) | Diabetes Type II | Race* | Pain Duration in Years (Range) |
|---|---|---|---|---|---|---|
| 0.1% | 61.2 (35-84) | 46.3% F | 13.3 (1-44) | 83.3% | 83.3% C, 9.3% B, 7.4% H | 5.5 (1-16) |
| 0.2% | 61.0 (30-84) | 55.6% F | 12.4 (1-44) | 84.2% | 77.8% C, 3.7% B, 14.8% H, 3.7% O | 5.6 (1-21) |
| Placebo | 61.2 (37-83) | 54.4% F | 10.5 (1-37) | 84.2% | 82.4% C, 8.8% B, 8.8% H | 4.4 (1-20) |

*C = Caucasian, B = Black, H = Hispanic, O = Other

A total of 14 patients dropped out of the study: 8 on 0.1% gel, 5 on 0.2% gel, and 1 on placebo. Results of a 3 factor (Investigator, Time and Treatment) repeated measures analysis of variance revealed no significant differences with respect to Time (p=1.00) or Investigator (p=0.598), and no significant interaction between Time and Treatment (p=0.817) and Treatment and Investigator (p=0.805).

Results

Patients randomized to 0.1% clonidine gel had a significantly greater reduction in NGPS averaged over time, compared to patients on placebo (Repeated Measures Analysis with last observation carried forward [LOCF] for any missing values p=0.015). Results from the analysis of averaged NGPS over time from patients in the 0.2% group compared to placebo was borderline significant (Repeated Measures Analysis with LOCF p=0.054). None of the secondary efficacy variables for clonidine treatment groups were significantly different from placebo. However, weekly averages of NGPS scores from the patient diaries, pain relief scores, and functional interference scores favored the active clonidine formulations.

Analgesia from 0.1% clonidine gel, compared to placebo, was demonstrated as early as the first week of treatment. At week 1, the mean change from baseline was −1.87 for the 0.1% clonidine group versus −0.59 for the placebo group (p=0.003). At one week following the discontinuation of treatment (week 9) analgesia continued with a mean change from baseline of −2.43 for the 0.1% clonidine group and −0.95 for the placebo group (p=0.009). The mean change in NGPS from baseline to final visit with the last observation carried forward to account for dropouts or missing visits was ∼1.96 for placebo, −2.52 for the 0.2% formulation and −2.96 for the 0.1% formulation. FIG. 1 shows the mean NGPS reduction by week.

There were no significant intra-patient differences in mean blood pressure or pulse observations, when comparing pre-treatment, during treatment and post-treatment. Likewise there were no significant differences between the three treatment groups. No rebound hypertension was observed following abrupt discontinuation of treatment.

Clonidine plasma concentrations were analyzed in a group of patients who completed the trial. A similar number of samples from a prior trial of 0.05% clonidine were also analyzed at the same time. Table 3 summarizes these results.

TABLE 3

Patient clonidine plasma concentrations

| Formulation | 0.05% | 0.1% | 0.2% |
|---|---|---|---|
| Daily Clonidine Dose | 2.5 | 3.9 | 6.0 |
| # Samples | 25 | 24 | 25 |
| # Samples with Measurable Clonidine Concentrations (>0.025 ng/ml) | 13 | 16 | 14 |
| Mean of Measurable Concentrations (ng/ml) | 0.0831 | 0.0749 | 0.0827 |
| Range of Measurable Concentrations (ng/ml) | 0.0290-0.286 | 0.0281-0.176 | 0.0346-0.177 |
| Mean Concentrations for All Samples | 0.0572 | 0.0589 | 0.0583 |

In conclusion, patients with painful diabetic neuropathy on 0.1% clonidine gel had a statistically significantly better analgesic response averaged over time (p=0.015) compared to the response for the placebo group. While the 0.2% clonidine gel was not statistically superior to placebo gel (p=0.054), the trend toward superiority is supportive for topical clonidine analgesia.

Further, plasma clonidine concentrations tended to be far below the threshold levels that are required for a antihypertensive effect (0.2 ng/ml). A lack of significant intra-patient or inter-group changes in blood pressure and a lack or rebound hypertension indicate that topical application of clonidine is relatively free of typical systemic clonidine adverse events.

Example 3

Single Dose Pharmacokinetic Study with 0.1% Clonidine Gel

Materials and Methods

Six volunteers applied single doses of 0.1% clonidine gel up to a maximum of 2 mg clonidine HCl per day. Clonidine plasma concentration analysis was conducted and consisted of a validated gas chromatography/mass spectroscopy method with a quantitative limit of 0.025% ng/ml.

Results

Clonidine plasma concentration analysis in the group of six volunteers showed all samples to be below the limit of quantitation. Therefore, single doses, even as large as 2.0 mg/day of 0.1% topical clonidine gel are insufficiently absorbed to have any antihypertensive effect or be of any clinical consequence.

Example 4

Multiple Dose Pharmacokinetic Study with 0.1% Clonidine Gel

Materials and Methods

This investigation was performed as an open-label, randomized, multiple-dose, two-treatment, crossover design study using 8 adult volunteers. The two treatments were: 1) application of 3.15 gm/day (3.1 mg clonidine HCl/day) (treatment A) of 0.1% clonidine gel delivered in three divided doses for 14 days on the right lower leg, and 2) application of 6.23 gm/day (6.2 mg clonidine HCl/day) (treatment B) of 0.1% clonidine gel delivered in three divided doses for 14 days on both lower legs. Treatment lasted for 14 days followed by a 7-day no-treatment observation period. Clonidine plasma concentration analysis was performed as in Example 3.

Results

Figure 2:
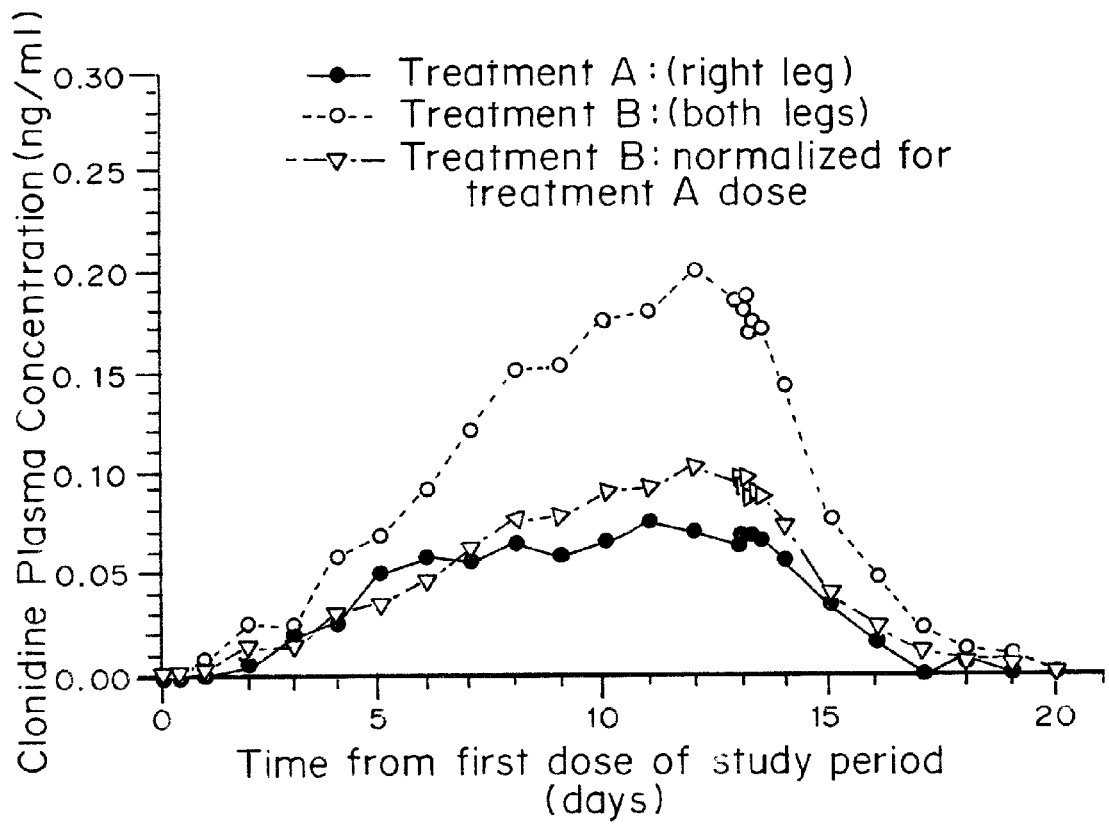
FIG. 2 is a graph of mean clonidine plasma concentrations over time from first dose (in days) of 0.1% clonidine for treatment A (dark circles): 3.15 g/day (3.1 mg clonidine HCl) and treatment B (open circles) 6.23 g/day (6.2 mg clonidine HCl).

Clonidine plasma concentration data following 14 days of controlled treatment in normal volunteers showed systemic absorption of clonidine after topical application was slow, incomplete, and variable among subjects. After initiation of therapy with the 0.1% topical clonidine gel, a time lag of 48 to 96 hours occurred before systemic absorption of clonidine was observed in the plasma. The mean (CV)$t_{lag}$ was 93.0 hours with treatment A and 78.0 hours with treatment B (p>0.1, A vs. B). After the lag time, clonidine plasma concentrations increased gradually until steady state was achieved between study days 11 and 13. Following the last dose, clonidine plasma concentrations declined with a mean (CV) elimination t½ of 38.5 hours for treatment A and 35.3 hours for treatment B (p>0.1). It took 7 days before the clonidine concentrations fell below the level of detection. FIG. 2 shows a plot of mean plasma concentrations as a function of time.

The apparent dose-dependent pharmacokinetics with topical clonidine gel is of limited clinical importance in view of the substantially lower steady-state plasma concentrations as compared to those reported following clinically applicable doses of oral and transdermal clonidine. The mean $C_{max}$ of 0.067 ng/ml during treatment A and 0.181 ng/ml during treatment B are both below the threshold of clonidine plasma concentrations associated with the drug's antihypertensive effects (0.2 ng/ml). Additionally, no clinically important changes in blood pressure or heart rate occurred in any subjects during the study.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described.

Those skilled in the art will recognize, or be able to ascertain using no more than routine experimentation, many equivalents to the specific embodiments of the invention described herein. Such equivalents are intended to be encompassed by the following claims.

I claim:

1. A method for the treatment of painful length dependent neuropathy that is not sympathetically maintained in a patient in need thereof and having functional pain signaling primary afferent (sensory) fibers and their receptors comprising locally or topically administering to a site at or adjacent to painful areas in the patient having functional pain signaling primary afferent (sensory) fibers and their receptors, an effective amount of an alpha2-adrenergic agonist at the site of administration and not systemically, to reduce or alleviate pain from length dependent neuropathy or other neuropathy that results in pain associated with disease or damage to the pain signaling primary afferent (sensory) fibers or their receptor, that is not sympathetically maintained pain, wherein the alpha2-adrenergic agonist is a compound having the structure represented by formula I:

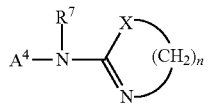

wherein $A^4$ may be selected from aryl, and heteroaryl, which may be substituted by one or more radicals selected from alkyl, branched alkyl, cycloalkyl, hydroxyl, alkoxy, cycloalkylalkyl, alkoxyalkyl, aryl, alkanoyl, alkoxycarbonyl, carboxyl, amino, cyano, halogen, thioalkyl, dialkylamino, arylamino, alkylsulfinyl, alkylsulfonyl, arylsulfinyl or arylsulfonyl; wherein X is selected from thio, imino, or methylene; wherein $R^7$ is selected from hydrogen, lower alkyl, or oxygen-containing heterocycle; and wherein n is either 2 or 3; or a pharmaceutically acceptable salt thereof.

2. The method of claim 1 wherein the compounds of Formula I consist of those compounds wherein $A^4$ is phenyl; wherein $A^4$ is substituted phenyl, on which positions 2 and 6 of the phenyl ring may be independently substituted by a radical selected from hydrogen, chloro, methyl, ethyl, or cycloalkyl, and positions 3, 4, and 5 may be independently substituted by a radical selected from hydrogen, methyl, trifluoromethyl, fluoro, or cyano; wherein $A^4$ is 3-thienyl, on which positions 2 and 4 are independently substituted by a radical selected from hydrogen, chloro, methyl, ethyl, or cycloalkyl; wherein $A^4$ is 1-naphthyl, 5,6,7,8-tetrahydronaphthyl-1-yl, pyrrolyl, oxazolyl, isoxazolyl, indol-3-yl, indazol-3-yl, quinolinyl, quinazolinyl, quinoxazolinyl, benzoxazolyl, and benzothiophen-3-yl; wherein $A^4$ is pyrimidin-4-yl, on which positions 3 and 5 are independently substituted by hydrogen, chloro, methyl, ethyl, cycloalkyl, or methoxy; wherein $R^7$ is either hydrogen or tetrahydropyran-2-yl; wherein X is thio or imino; and wherein n is 2.

3. The method of claim 1 wherein the compound is selected from the group consisting of compounds wherein $A^4$ is selected from phenyl, 2,6-dichlorophenyl, 2,6-dimethylphenyl, 2,6-diethylphenyl, 3,4-dihydroxyphenyl, 3-fluoro-6-methylphenyl, 2-chloro-5-trifluoromethylphenyl, 2-chloro-4-methylphenyl, 3-chloro-4-methylthien-3-yl, 5,6,7,8-tetrahydronaphth-1-yl, and 4-chloro-5-methoxy-2-methylpyrimidin-4-yl; wherein $R^7$ is hydrogen or tetrahydropyran-2-yl; wherein X is thio or imino; and wherein n is 2.

4. The method of claim 1 wherein the compound is selected from the group consisting of xylazine, flutonidine, moxonidine, tramazoline, tolonidine, piclonidine, tiamenidine, and clonidine.

5. The method of claim 1 wherein the compound is formulated in a carrier for topical administration.

6. The method of claim 1 wherein from 0.01% to 1.0% clonidine is applied to the painful area affected by the neuropathy.

7. The method of claim 1 wherein the clonidine is given from once a week to several times a day.

8. The method of claim 1 wherein the treatment is given to patients with neuropathy that stems from diabetes mellitus.

9. The method of claim 1 wherein the treatment is administered to patients with a sensory peripheral neuropathy in the painful region.

10. The method of claim 1 wherein the treatment is administered to a patient with a small fiber neuropathy in the painful region.

11. The method of claim 1 further comprising administering a therapy selected from the group consisting of opioids, anticonvulsants, membrane stabilizers, and psychoactive drugs such as anti-depressants.

12. The method of claim 4 wherein the compound is clonidine.

13. The method of claim 5 wherein the topical carrier is selected from the group consisting of transdermal patches, gels, ointments, lotions, liposomal formulations, creams, and emulsions.

14. The method of claim 4 wherein the concentration of clonidine is between 0.1 and 10% clonidine.

* * * * *